United States Patent [19]

Barnes

[11] Patent Number: 5,062,847
[45] Date of Patent: Nov. 5, 1991

[54] LAPAROSCOPIC RETRACTOR

[76] Inventor: William E. Barnes, P.O. Box 126, Salem, Ky. 42078

[21] Appl. No.: 636,482

[22] Filed: Dec. 31, 1990

[51] Int. Cl.$^5$ .............................................. A61L 17/11
[52] U.S. Cl. ..................................... 606/194; 604/107
[58] Field of Search ................... 128/20; 604/104–109; 606/191, 198

[56] References Cited

U.S. PATENT DOCUMENTS

| | | | |
|---|---|---|---|
| 1,434,964 | 11/1922 | Rose | 604/108 |
| 1,636,969 | 7/1927 | Rose | 604/107 |
| 3,495,586 | 2/1970 | Regenbogen | 606/198 |
| 3,667,474 | 6/1972 | Lapkin et al. | 606/198 |
| 4,585,000 | 4/1986 | Hershenson | 604/108 |
| 4,648,402 | 3/1987 | Santos | 606/198 |
| 4,654,028 | 3/1987 | Suma | 604/106 |
| 4,909,789 | 3/1990 | Taguchi et al. | 604/107 |
| 4,936,823 | 6/1990 | Colvin et al. | 604/106 |

Primary Examiner—Stephen C. Pellegrino
Assistant Examiner—Ralph A. Lewis
Attorney, Agent, or Firm—Paul B. Overhauser

[57] ABSTRACT

The invention comprises a surgical retractor having a barrel with a distal end and a handle. A plurality of retractor pods are located at a plurality of angles and positions on the lateral periphery of the barrel. The retractor pods are movable between a retracted position in which the pods are substantially flush with the surface of the barrel and an extended position in which each pod outwardly and laterally projects from the barrel. The handle is operatively connected to the pods to move the pods between the retracted and extended positions.

4 Claims, 2 Drawing Sheets

LAPAROSCOPIC RETRACTOR

FIELD OF THE INVENTION

The present invention relates to surgical retractors, and in particular, to surgical retractors suitable for laparoscopic surgery.

BACKGROUND OF THE INVENTION

During surgery, particularly surgery in the abdominal cavity, it is necessary to employ surgical retractors to position organs to provide suitable access to the surgical site. Moreover, the required recovery period following surgery is often directly proportional to the size of the incision(s) made during surgery. Accordingly, laparoscopic surgery, which typically requires that only several small (1 cm.) incisions be made, is an increasingly utilized form of surgery because the recovery period is significantly reduced. Because the incisions made for laparoscopic are very small, manipulation of the surgical instruments, including retractors, at the surgical site is a very difficult and precise task. In particular, conventional surgical retractors are far too large to be passed through trocars used for laparoscopic surgery. In addition, retractors which may be narrow enough to be passed through a laparoscopic trocar often retract tissue in a direction extending from the tip of the retractor. However, it is often necessary to retract tissue in a number of different directions lateral to the body of the retractor.

These problems are not solved by known surgical instruments. For example, U.S. Pat. No. 4,909,789 discloses a forceps which act as a retractor for pushing aside tissue for improved observation. The device may be used with an endoscope, arthroscope or similar device. internally, three wires with rounded ends are contained within a barrel. The wires are spring biased in the retracted mode until pressure is applied to a plate, forcing the wires outwardly and diverging. A set screw may be adjusted to maintain the wire position. However, the retractors are forced out the end of the barrel, as opposed to the sides.

U.S. Pat. No. 4,654,028 discloses a tissue expander device. An elongated barrel houses a wire which emerges as three round ended wires at the end of the barrel. When energized, the wires expand in three dimensions thereby displacing soft tissue for improved visualization. This device is intended for use primarily for blood vessel graft surgery, as opposed to laparoscopic surgery. U.S. Pat. No. 1,878,671 discloses a dilator for drainage. A hollow shaft houses an elongated rod with an oblong head. When the rod is pushed in, the elongated head is displaced to the side so as to dilate surrounding tissue. Again, this device operates from the end of the barrel as opposed the side.

U.S. Pat. No. 4,655,219 discloses a multi-component grasping device. A plurality of wires with hooked ends are forced outward when engaged and close around the desired object when the wire is retracted. This device is not intended to be used as a retractor, and again, the wire ends are enjected from the tip of the barrel as opposed to the sides.

U.S. Pat. No. 4,705,041 discloses a dilator for the sphincter of oddi. A single rod is contained within a catheter and ends as a scissors-like mechanism. Retraction of the handle forces the central wire against the scissors mechanism forcing it open and expanding the region of interest. However, expansion occurs only in one plane perpendicular to the shaft, so tissue expansion is minimized.

OBJECTS OF THE INVENTION

Accordingly, it is an object of the invention to provide a surgical retractor suitable for use during laparoscopic surgery.

It is a further object of the invention to provide a surgical retractor which laterally retracts tissue at all angles from the sides of the barrel of the retractor.

It is further an object of the invention to provide a surgical retractor which maximizes the retractor surface area so as to minimize the rick of injury to retracted tissue.

It is a further object of the invention to provide a surgical retractor which retracts tissue along a plurality of positions along the length of the barrel of the retractor.

It is a further object of the invention to provide a surgical retractor which has a rounded end to minimize injury to tissue.

SUMMARY OF THE INVENTION

The invention comprises a surgical retractor having a barrel with a distal end and a handle, a plurality of retractor pods located at a plurality of angles and positions on the lateral periphery of the barrel, the retractor pods being movable between a retracted position in which the pods are substantially flush with the surface of the barrel and an extended position in which each pod is outwardly and laterally projected from the barrel, the handle means being operatively connected to the pods to move the pods between the retracted and extended positions.

DETAILED DESCRIPTION

Figure 1:
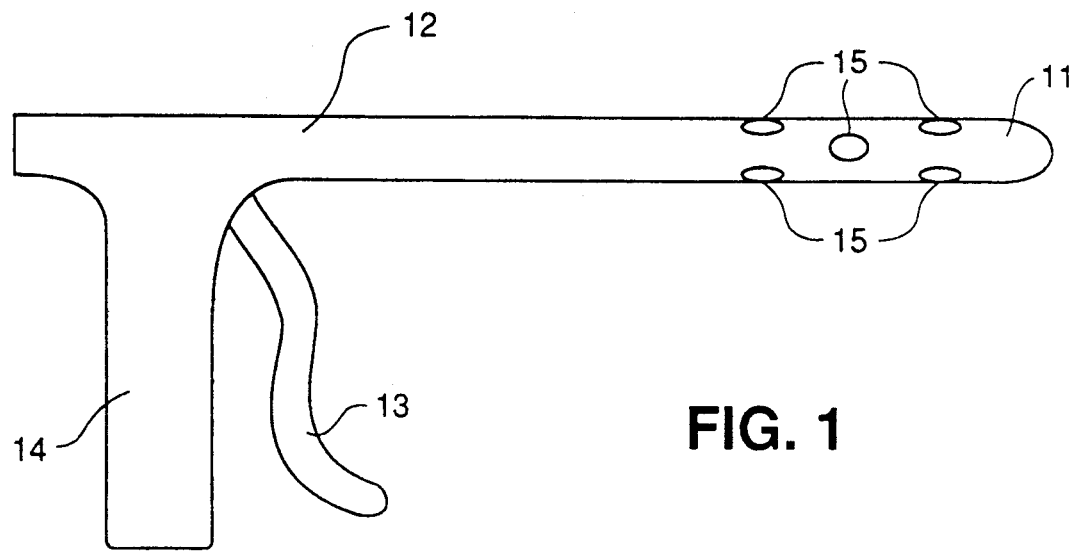
FIG. 1 is a side view of the invention showing the retractor pods in a retracted position.

Referring to FIG. 1, there is shown one embodiment of the invention, which comprises barrel 12 of about 32 centimeters in length having a distal end 11, and which may be made from, for example, molded plastic such as polyethylene of polystyrene. At the opposite end of barrel 12 is handle 14, which includes trigger 13. Laterally disposed on the periphery of barrel 12 are a plurality of retractor pods 15, which are located at a plurality of angles with respect to the axis of barrel 12 and which are flush with barrel 12 when in their retracted position as shown in FIG. 1. Retractor pods 15 may be made from the same plastic as barrel 12, or alternatively, they may be manufactured from a softer material such as pliable plastic, rubber or latex, so as to minimize the risk of injury to delicate tissue during retraction.

Figure 2:
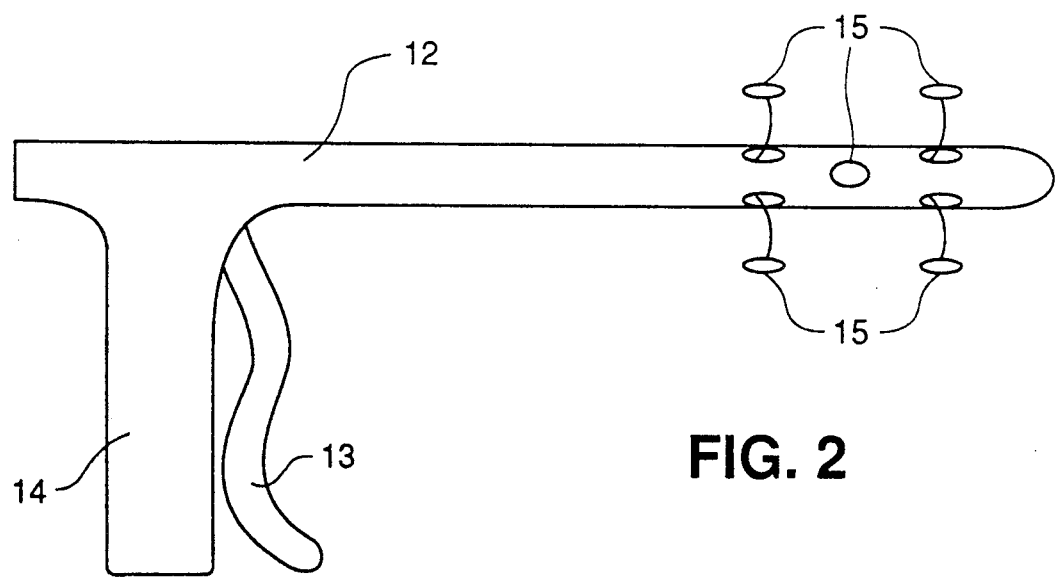
FIG. 2 is a side view of the invention showing the trigger depressed and the retractor pods in their extended position.

As shown in FIG. 2, when trigger 13 is depressed, retractor pods 15 are forced laterally outward from the barrel to an extended positio by resilient fibers 16. It will be appreciated that during surgery, the movement of retractor pods 16 in the outward lateral direction will retract tissue adjacent to the sides of the barrel at all angles. Such retraction is particularly useful during laparoscopic surgery as the maneuverability during such surgery does not permit positioning of retractors as easily as during conventional open surgery. To permit insertion of barrel 12 through a trocar, the width of barrel 12 is perferably 1 centimeter or less.

Figure 3:
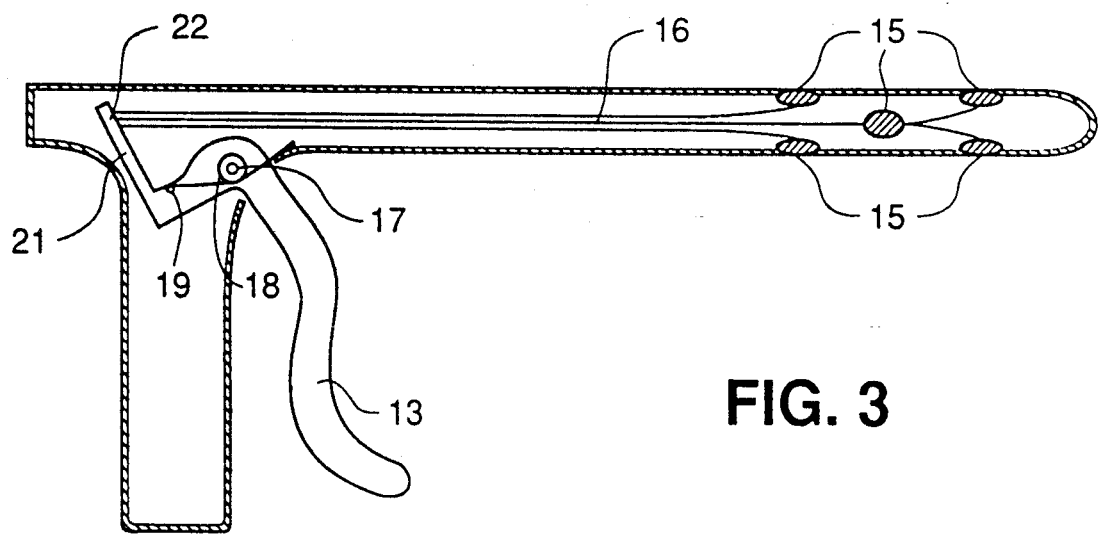
FIG. 3 is a side sectional view of the invention showing the connections between the pods and the trigger.

FIG. 3 is a side sectional view of one embodiment of the invention showing how fibers 16 connect trigger 13 to pods 15. Fibers 16 may be comprised of relatively stiff, yet flexible and resilient, plastic strands, such as those used in hair brushes. In the preferred embodiment, fibers 16 are curved so that when trigger 13 is pulled, the naturally force pods 15 outward and laterally from the axis of barrel.

Figure 4:
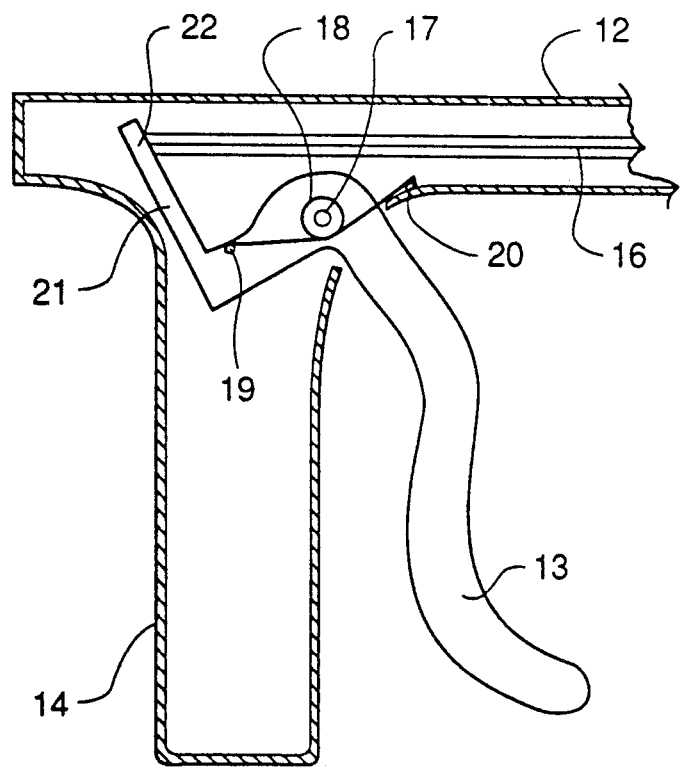
FIG. 4 is a partial side section view showing the trigger spring biasing the trigger.

FIG. 4 is a partial side section view showing how trigger 13 is biased to hold pods 15 in their retracted position by spring 18. Trigger 13 is pivotable about pivot point 17. Spring 18 fits at one end around the upper edge of trigger lever 21 at a point 19, and at the opposite end, against barrel 12 at point 20. Thus, spring 18 biases trigger towards its unactuated position, holding fibers 16 and pods 15 in their retracted position.

I claim:

1. A surgical retractor comprising
   a barrel having a distal end and handle located opposite the distal end of said barrel,
   a plurality of retractor pods located at a plurality of angles and positions on the lateral periphery of the barrel,
     the retractor pods being movable between a retracted position in which the pods are substantially flush with the surface of the barrel and an extended position in which each pod is outwardly and laterally projected from the barrel.
   the handle being operatively connected to the pods to move the pods between the retracted and extended positions, wherein the handle comprises a trigger and a grasping member, the trigger being pivotable with respect to the grasping member, and further comprising
   flexible, resilient fibers positioned substantially within the barrel having opposite ends connected to the trigger at one end and to a retractor pod at the opposite end.

2. The surgical retractor of claim 1 wherein the fibers are biased toward curving outward from the surface of the barrel.

3. The surgical retractor of claim 1 further comprising bias means for biasing the trigger and the fibers so the retractor pods are in the retracted position.

4. The surgical retractor of claim 3 wherein the bias means comprises a spring.

* * * * *